United States Patent
Rowland

Patent Number: 6,096,032
Date of Patent: Aug. 1, 2000

[54] MEDICAL CRYO-SURGICAL DEVICE

[76] Inventor: Stephen James Rowland, 38 Broomhill Road, Old Whittington, Chesterfield, S41 9DA, United Kingdom

[21] Appl. No.: 09/242,276
[22] PCT Filed: Aug. 12, 1997
[86] PCT No.: PCT/GB97/02177
 § 371 Date: Feb. 12, 1999
 § 102(e) Date: Feb. 12, 1999
[87] PCT Pub. No.: WO98/06339
 PCT Pub. Date: Feb. 19, 1998

[30] Foreign Application Priority Data

Aug. 14, 1996 [GB] United Kingdom ............... 9617034

[51] Int. Cl.[7] .................................................. A61B 18/18
[52] U.S. Cl. ................................ 606/20; 606/21; 606/22; 606/23
[58] Field of Search .................. 606/20–26; 607/96–101

[56] References Cited

U.S. PATENT DOCUMENTS

| | | | |
|---|---|---|---|
| 4,440,167 | 4/1984 | Takehisa | 606/20 |
| 4,519,389 | 5/1985 | Gudkin et al. | 606/20 |
| 4,646,735 | 3/1987 | Seney | 606/22 |
| 5,139,496 | 8/1992 | Hed | 606/23 |
| 5,207,674 | 5/1993 | Hamilton | 606/20 |
| 5,733,280 | 3/1998 | Avitall | 606/23 |

*Primary Examiner*—John P. Leubecker
*Assistant Examiner*—David M. Ruddy
*Attorney, Agent, or Firm*—Trexler, Bushnell, Giangiorgi & Blackstone, Ltd.

[57] ABSTRACT

The invention relates to a medical cryo-surgical device. Hitherto, such devices have employed the Joule-Thompson cooling effect, liquid nitrogen, or a sprayed volatile liquid. All such devices will serve the required purpose of cooling tissue to the level that will cause ice crystal formation, but all are relatively inefficient. The invention seeks to provide an improved device, an objective met by a construction comprising a primary heat extraction means (1), a secondary heat extraction means (12) associated with a part to be applied to a patient, and a coolant circuit (14) connecting the primary and secondary heat extraction means. The heat extraction means may be thermo-electric devices that can be sequentially or concurrently activated.

9 Claims, 1 Drawing Sheet

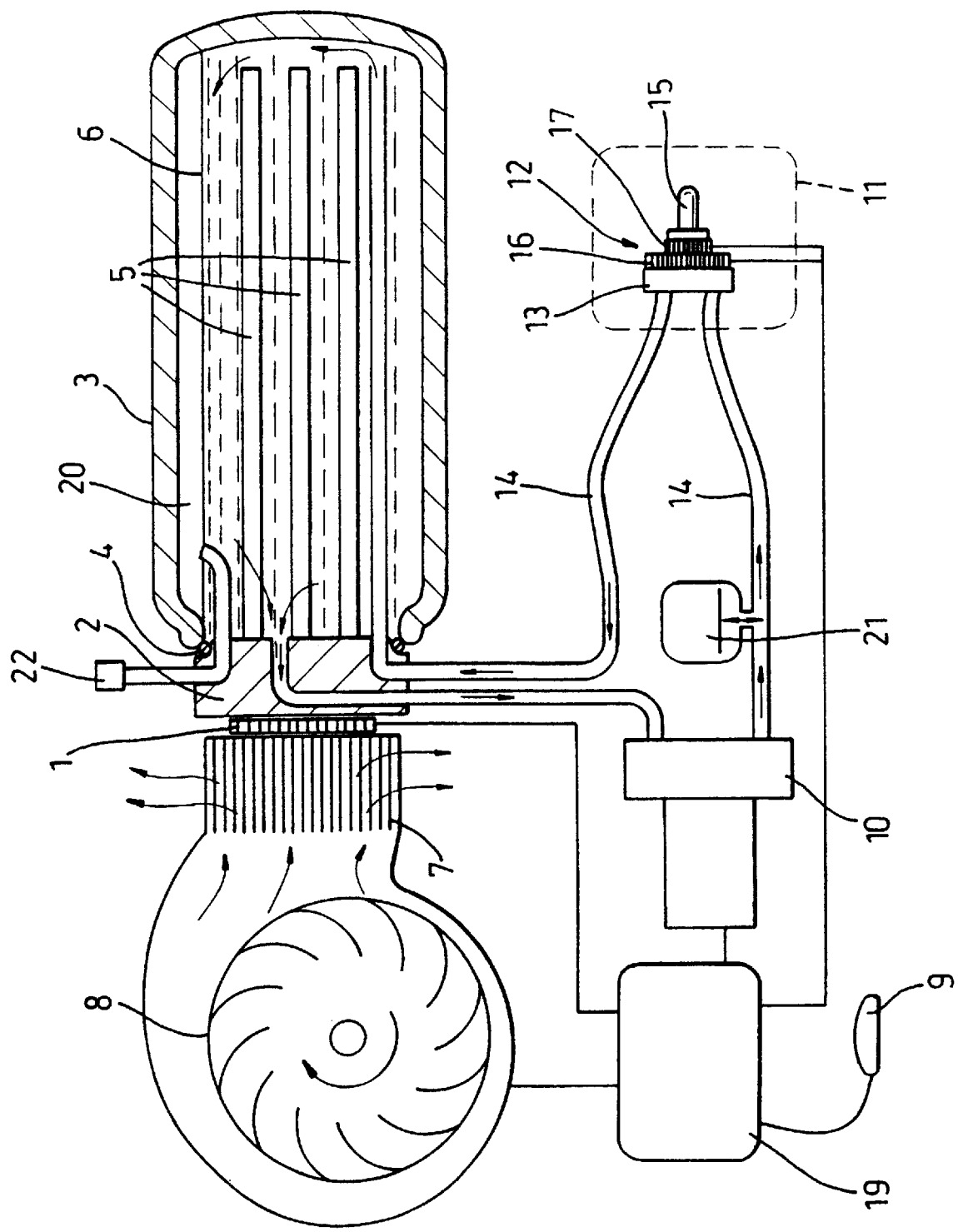

MEDICAL CRYO-SURGICAL DEVICE

This invention relates to a medical cryo-surgical device.

Warts and other dermatological conditions may be treated by the application of intense cold. This freezing has to be sufficiently sever to form ice crystals within the tissue being treated. At present this cooling is usually accomplished by one of the following methods:

(1) When a gas is expanded adiabatically, through a porous plug, the gas will cool down and it will cool down the plug as well. This cooling is known as the Joule-Thompson effect. The gases that are used in practice are either carbon dioxide or nitrous oxide.
(2) Liquid nitrogen at its boiling point of −196 degrees Celsius may be applied to the tissue to be treated either directly or by using the liquid to cool an applicator.
(3) As a liquid evaporates the liquid that remains will cool down. Spraying a volatile liquid onto the tissue, either directly or through porous applicator, will cause the tissue to cool down.

These three basic processes have various advantages and disadvantages.

In the system using the Joule-Thomson effect a temperature of about −40 degrees C. is reached quite rapidly and there is good thermal contact between the porous plug and the tissue under treatment. It is also possible to limit the cooling to a specific area. The system does have the disadvantage that a heavy carbon dioxide or nitrous oxide cylinder is needed to power the device. The cylinders also need replacing as the gas is used up. Changing cylinders requires a certain amount of skill and strength to ensure that there are no leaks and that the threads are not crossed or damaged.

Liquid nitrogen, although having a very low boiling point (−196 degrees C.) Is difficult to apply only to the tissue to be treated because the liquid can splash onto surrounding areas thereby resulting in frost burns. When the liquid touches the warm skin a thin, insulating layer of gaseous nitrogen is formed which limits its cooling effect. The use of liquid nitrogen is generally limited to hospitals that have a regular supply for other purposes. The liquid nitrogen is also continuously evaporating and cannot be stored for any length of time.

Using an evaporating volatile liquid tends not to cool the tissue sufficiently to destroy it effectively. This method does however have the advantage of being readily available in easily transportable spray canisters.

To extend the availability of cryo-surgery it would be advantageous to have a suitable piece of equipment that would quickly and reliable cool down the treated tissue but have none of the disadvantages of the methods in present use. Obviously a portable device that could be operated from the mains electrical supply, without requiring any consumable supplies, would have very distinct advantages over the present methods. Such a piece of equipment would allow patients to be treated in Family Practitioners' surgeries rather than hospital based facilities.

Thermoelectric devices where two dissimilar metals are joined together to form a circuit and the junctions were maintained at different temperatures to cause a current flow have been known for a considerable number of years. The reverse of this process was discovered by the French physicist Jean Peltier who observed that if a current was passed through two different metal conductors, a temperature difference could be maintained at the junctions. Heat called the Peltier heat, is either absorbed or emitted at the junction depending on the direction of current flow. It was subsequently demonstrated that it was possible to freeze a droplet of water by using a bismuth-antimony junction with a current flowing in one direction and melting the frozen droplet by reversing the current flow.

This so-called Seebeck effect was put to practical use to make the familiar thermocouple thermometer. However, the Peltier effect was of little practical use, as metals, while being good conductors of electricity are also good conductors of heat. Because the Peltier heat was quickly conductor between the junctions, little temperature difference could be maintained. It was not until suitable semiconductor materials were developed that a Peltier cooler could become a practical proposition. In 1963 a junction of N and P type bismuth telluride ($Bi_2 Te_2$) was found to have large Seebeck coefficient combining good electrical conductivity with low thermal conductivity. A practical refrigeration element could now be made by connecting these junctions electrically in series and thermally in parallel.

Although first developed in he 1960's these thermoelectric cooling devices were quite costly and their main use was for cooling infrared detectors in satellites. Over the past few years their cost has been reduced considerably and the type used in the proposed invention cost between 20 and 30 pounds each, thus making a cryo-probe a cost effective proposition. The thermoelectric cooling device is outwardly relatively simple compared to a conventional refrigerator with its pumps and pipework but there are substantial difficulties in using these devices to achieve the low temperature to −50 to −60 degrees C. require for effective use as a cryo-surgical device.

For the device to be built into free-standing, mains operated piece of equipment the final waste heat will need to be transferred to the air at a room temperature of about 20 degrees C. A practical heat exchanger would be required to operate at 10 to 15 degrees C. above this and so a temperature of 30 to 35 degrees C. would have to be allowed for one the hot side of the thermoelectric cooling device. Therefore, to achieve a probe tip temperature of −60 degrees C. a temperature difference of 90 to 95 degrees C. would have to be maintained. The manufacturers of thermoelectric cooling devices quote a maximum temperature difference (delta T) for a single stage cooler of about 60 degrees C. This is the maximum measured in high vacuum with no heat flow. When a larger heat load is applied to the cooler (as in a cryo-surgical situation) the delta T across the device will drop rapidly. In practice it is possible to stack the coolers one on top of another but there are difficulties attendant upon this. The main difficulty is the increased waste heat (generated by the electrical resistance of the semiconductors) that has to be pumped by the subsequent stage coolers so the gains provided by stacking become quickly progressively less. Also in order to achieve optimal performance of a stacked system the current flows to the stages would need to be calibrated and this would vary with both heat load and duration of use.

Representative of the prior art of particular relevance to the present invention are WO-A-92/20289 and FR-A-2 613 611. WO-A-92/20289 discloses a medical cryo-surgical device having a primary heat extraction means for coolant and a secondary heat extraction means associated with the part of the device adapted for application to a patient, with a coolant circuit connecting the primary and secondary heat extraction means. FR-A-2 613 611 similarly deals with a cryo-surgical device displaying a series of stacked thermoelectric modules electrically linked together in series and operating via direct current, and having a heat exchanger associated with the hot face of the first module of the series. Here the heat output generated by each module decreases from the first module to the last module with which is associated that part of the device to be applied to a patient.

The object of the present invention is to provide an improved medial cryo-surgical device.

According to the present invention, a medical cryo-surgical device comprises a primary heat extraction means, and a secondary heat extraction means associated with a part adapted for application to a patient, and there being a coolant circuit connecting the primary and secondary heat extractions means.

The primary heat extraction means may be located in a main housing, and the said part to be applied to a patient and the secondary heat extraction means may be located in a hand set, with the coolant circuit connecting the main housing to the hand set.

Most desirably, the said primary and secondary heat extraction means are formed by thermoelectric devices, with switch means to activate the thermoelectric devices sequentially or concurrently.

The primary thermoelectric cooling device is used to cool a coolant solution housed within the main unit. This coolant can then be circulated to the hand set by switch means. The coolant is thereby used to cool the hot side of the secondary thermoelectric cooling device housed within the hand set. The thermoelectric cooling device within the hand set is activated by switch means either subsequent on or concurrent with the circulation of the pre-cooled coolant solution. This thermoelectric cooling device is then used to cool the patient applied part. This two stage approach allows the possibility of switching off the current to the primary thermoelectric cooling device when the secondary thermoelectric cooling device is activated and also circumvents the problems attendant upon the increased waste heat dissipation that would be incurred by simple stacking of thermoelectric cooling devices as outlined above. This approach relies on the fact that the application of cryo-therapy is of short duration relative to the time between applications and that in the time between applications the secondary thermoelectric cooling device is switched off and current flows solely to the primary thermoelectric cooling device thereby recooling the coolant.

One embodiment of the invention will now be described by way of example by reference to the accompanying drawing, which is a schematic representation of a medical cryo-surgical device.

Referring to the drawing, the coolant thermoelectric cooling device (primary thermoelectric cooling device) (1) will begin to remove the heat from a brass cooling block (2) when the equipment is switched ON. This cooling block is mounted on to the neck of a 750 ml stainless steel Dewar flask (3) and sealed with an 'O' ring (4). Into this brass block are soldered a number of solid copper rods (5) which will conduct the heat away from the coolant (6) which is stored inside the Dewar vessel.

The coolant used is a mixture of 30% (Ethylene glycol ) and 70% water (by volume). At this concentration the coolant will remain useable down to a temperature of −20 degrees C. The waste heat is removed by a highly efficient heat exchanger (7) with a good thermal efficiency when it is cooled with an air blower (8). The coolant will be cooled down to approximately −5 degrees C. in about 30 to 40 minutes depending on ambient air temperature. The flask (3) is mounted horizontally and because of the shape of the neck a small amount of air will be trapped at the top. This air space acts as an expansion/contraction chamber (20). A filling vent and pressure release value (22) are fitted as shown to facilitate filling with coolant and allow eflux of coolant should pressure build up within the system due to abnormal ambient conditions In order to commence cryo-surgical treatment the air actuated momentary foot switch (9) is pressed and this switches [via the electrical power supply and control unit (19)] on the low voltage coolant pump (10) and the hand set (11) thermoelectric cooling devices (12). The switch (9) will also switch off the current to the primary thermoelectric cooling device (1).

This pump (10) will now pump the already pre-cooled coolant (6) to the hand set (11). through the hand set heat exchanger (13), and back to the flask (3) in a closed circuit via pipes (14). A ballast chamber (21) is incorporated in the circuit on the outlet side of the pump (10) to eliminate any pulsatile flow that may affect operator efficiency.

The hand set (11) has a treatment tip (15) made of copper (plated to prevent corrosion) which is applied to the treatment lesion via conductive jelly. Inside the hand set is a two-stage thermoelectric cooling device (16) and (17) (secondary thermoelectric cooling device. The waste heat from the second stage device (16) is removed by the coolant (6) via the finned heat exchanger (13). This heat exchanger has a labyrinthine duct to ensure good thermal efficiency. The electrical power to the first stage thermoelectric cooling device (17) of the secondary thermoelectric cooling device has been adjusted to give optimum performance, as too much power will only result in more waste heat having to be pumped by the second stage thermoelectric cooling device (16).

After the treatment of approximately one to two minutes duration, the hand set (11) and pump (10) are switched off by releasing the momentary foot switch (9). The coolant, having absorbed the waste heat from the hand set, will have warmed up by approximately 5 degrees C.

When the hand set is not in use, in between cryo-surgical treatments, the primary thermoelectric cooling device (1) will then cool down the coolant ready for the next application.

What is claimed is:

1. A medical cryo-surgical device comprising a primary heat extraction means (1) for extracting heat from a coolant;

A secondary heat extraction means (12) associated with a patient applicator (15);

A coolant circuit (14) connecting the primary and secondary heat extraction means;

Said primary heat extraction means being formed of a thermo-electric device located on a brass block (2), said brass block being positioned in an inlet of a housing (3) which forms part of the coolant circuit;

cooper rods (5), which extend into the housing, located on the brass block;

a heat exchanger (7) associated with the thermo-electric device; and an air blower (8) associated with the heat exchanger.

2. A medical cryo-surgical device comprising a primary heat extraction means (1) for extracting heat from a coolant;

A secondary heat extraction means (12) associated with a patient applicator (15);

A coolant circuit (14) connecting the primary and secondary heat extraction means;

Said primary heat extraction means being formed of a thermo-electric device located on a conductive metal block (2), said conductive metal block being positioned in an inlet of a housing (3) which forms part of the coolant circuit;

Conductive metal rods (5), which extend into the housing, located on the brass block;

a heat exchanger (7) associated with the thermo-electric device; and an air blower (8) associated with the heat exchanger.

3. A medical cryo-surgical device as in claim 1 or claim 2 characterised in that the primary heat extraction means (1) is located between the heat exchanger (7) and the housing (3), and the secondary heat extraction means (12) is disposed in a handset (11).

4. A medical cryo-surgical device as in claim 1, characterised in that the secondary heat extraction means (12) is formed by a thermelectric device.

5. A medical cryo-surgical device as in claim 4 characterised by a switch means to activate the primary and secondary heat extraction means sequentially or concurrently.

6. A medical cryo-surgical device as in claim 1, characterised by a pump means (10) associated with the coolant circuit and control means (19) associated with the pump means (10), wherein the control means (19) is configured to operate the pump means (10) to drive the coolant round the coolant circuit (14).

7. A medical cryo-surgical device as in claim 1, characterized by a ballast chamber (21) in the coolant circuit to eliminate the pulsing of coolant supply to the secondary heat extraction means (12).

8. A medical cryo-surgical device as in claim 1, wherein the patient applicator (15) is a copper rod.

9. A medical cryo-surgical device as in claim 1, characterised in that the secondary heat extraction means (12) is a two stage thermoelectric device (16, 17), on stage (17) having located thereon the patient applicator (15), and the other part (16) having an associated heat exchanger (13) the heat-exchanger forming part of the coolant circuit.

* * * * *